(12) United States Patent
Seidling et al.

(10) Patent No.: US 9,357,771 B2
(45) Date of Patent: Jun. 7, 2016

(54) FOAMING SANITIZING FORMULATIONS AND PRODUCTS INCLUDING A QUATERNARY AMMONIUM COMPOUND

(71) Applicant: KIMBERLY-CLARK WORLDWIDE, INC., Neenah, WI (US)

(72) Inventors: Jeffery Richard Seidling, Appleton, WI (US); Corey Thomas Cunningham, Larsen, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 170 days.

(21) Appl. No.: 13/716,562

(22) Filed: Dec. 17, 2012

(65) Prior Publication Data

US 2014/0171513 A1    Jun. 19, 2014

(51) Int. Cl.
*A01N 25/16* (2006.01)
*A01N 33/12* (2006.01)

(52) U.S. Cl.
CPC ............... *A01N 25/16* (2013.01); *A01N 33/12* (2013.01)

(58) Field of Classification Search
CPC ............................. A01N 25/16; A01N 33/12
USPC ......... 424/47, 405; 514/642, 643; 516/10, 15, 516/17
See application file for complete search history.

(56) References Cited

U.S. PATENT DOCUMENTS

| 4,100,324 | A | 7/1978 | Anderson et al. | |
|---|---|---|---|---|
| 5,173,216 | A | 12/1992 | Uhlig | |
| 5,284,703 | A | 2/1994 | Everhart et al. | |
| 5,350,624 | A | 9/1994 | Georger et al. | |
| 7,670,615 | B2 | 3/2010 | Veeger et al. | |
| 2003/0008791 | A1 | 1/2003 | Chiang | |
| 2003/0069317 | A1* | 4/2003 | Seitz et al. | 514/731 |
| 2005/0169880 | A1 | 8/2005 | Glick et al. | |
| 2006/0205619 | A1* | 9/2006 | Mayhall et al. | 510/130 |
| 2006/0292086 | A1* | 12/2006 | Curtis | 424/47 |
| 2007/0258911 | A1 | 11/2007 | Fernandez de Castro et al. | |
| 2008/0207767 | A1 | 8/2008 | Dobos et al. | |
| 2010/0160452 | A1 | 6/2010 | Busby et al. | |
| 2011/0104079 | A1* | 5/2011 | Snyder et al. | 424/45 |
| 2013/0090380 | A1* | 4/2013 | Heisig et al. | 514/517 |

FOREIGN PATENT DOCUMENTS

| CA | 2468543 A1 | 11/2005 |
|---|---|---|
| JP | 2005154360 A | 6/2005 |
| WO | 0121138 A1 | 3/2001 |
| WO | 2009050447 A2 | 4/2009 |
| WO | 2009101409 A1 | 8/2009 |

OTHER PUBLICATIONS

International Search Report and Written Opinion of PCT/IB2013/060020, mailed Feb. 25, 2014.

* cited by examiner

*Primary Examiner* — Robert Jones, Jr.

(74) *Attorney, Agent, or Firm* — Armstrong Teasdale LLP

(57) ABSTRACT

Foaming formulations including a quaternary ammonium compound and a foam stabilizer are disclosed. These foaming formulations are useful as leave-on liquid hand and surface sanitizers. The foaming formulations provide improved aesthetic properties and foaming appearance, while maintaining high antimicrobial capacity.

20 Claims, No Drawings

FOAMING SANITIZING FORMULATIONS AND PRODUCTS INCLUDING A QUATERNARY AMMONIUM COMPOUND

BACKGROUND OF THE DISCLOSURE

The present disclosure relates generally to a formulation comprising a quaternary ammonium compound and a foam stabilizer. The combination of a quaternary ammonium compound and foam stabilizer provides antimicrobial effects without the use of alcohol while providing the formulation with improved foaming properties. The foaming formulations of the present disclosure are useful as cleansing formulations such as used in leave-on liquid hand and surface sanitizers.

According to the Center for Disease Control, proper cleansing can be one of the most effective steps taken to prevent the spread of diseases and infections. Specifically, proper bodily cleansing according to various sources requires not only using soap but also washing for a sufficiently long period of time in order to remove dirt and any microorganisms that may be present on the skin. For example, the Center for Disease Control has stated that effective cleansing should last at least 15 seconds.

As many consumers fail to effectively cleanse using soaps, alcohol-based sanitizing solutions and cleansing wipes capable of providing effective antimicrobial sanitization for hand or body cleansing purposes have been developed. Various forms of alcohol-based antimicrobial compositions are known in the art and have been used in the healthcare industry, food service industry, and private sector by individual consumers to provide a convenient means to control and prevent the spread of potentially harmful bacteria and other microorganisms. The alcohol-based antimicrobial compositions and cleansing wipes including the compositions are typically utilized to cleanse the skin by destroying bacteria and other microorganisms present thereon, especially on the hands, arms, and face of the user. Further, cleansing wipes, such as baby wipes, are used to cleanse the sensitive skin of infants.

While providing effective cleansing of the skin, frequent use of alcohol-based antimicrobial compositions and cleansing wipes including the compositions may cause skin irritation and dryness. This can be a problem for health care professionals, child care providers, food service workers and others who use these alcohol-based products to cleanse or sanitize their body multiple times in a day.

In view of this, sanitizing formulations have been developed including alternatives to alcohol. Several ingredients commonly used in these sanitizing formulations, such as many anionic high-foaming surfactants, however, have been found to negatively impact the antimicrobial efficacy and stability of the alcohol alternatives. To counteract this, higher levels of lower-foaming surfactants have been used to generate the dense foam associated with these types of sanitizing formulations. These high loads of surfactants, however, can lead to unpleasant skin feel, more expensive formulations, can be irritating to the skin, and depending on the surfactant, a negative impact on the antimicrobial activity.

Accordingly, there is a need for foaming formulations and cleansing products including the foaming formulations that provide effective skin cleansing and sanitizing effects, while having good foam stability. It would further be advantageous if the foaming formulations and products provided improved aesthetic properties and foaming appearance, while maintaining high antimicrobial activity.

BRIEF DESCRIPTION OF THE DISCLOSURE

It has now been unexpectedly found that improved foaming formulations effective for cleansing and sanitizing animate and inanimate surfaces can be formed with the use of a combination of a quaternary ammonium compound and a foam stabilizer. Particularly, although some sanitizing compositions containing certain alternatives to alcohol, such as quaternary ammonium compounds, provide some amount of foaming when used with a standard foaming pump engine, the foam that is generated begins breaking down immediately upon dispensing. The rapid drainage and dissipation of the bubbles reduces the ability of the foaming formulation, or foaming product, to stay where it is placed on the hand as the degradation of the bubbles causes the composition to change into its watery constituent solution.

It has now been unexpectedly discovered that the addition of a very small amount of a compatible foam stabilizing agent in a foaming formulation including a quaternary ammonium compound as an antimicrobial agent allows the bubbles to maintain their form and stay on the hand of the user until the user rubs the foaming formulation onto their hands in a manner appropriate to a hand sanitizing product. Further, it has been discovered that the combination of the quaternary ammonium compound and the foam stabilizers of the present disclosure provide enhanced skin aesthetics (e.g., substantivity while formulation is in use, reduced tackiness during and after formulation use, soft and conditioned skin feel of formulation, and improved foam appearance).

Accordingly, the present disclosure is directed to a foaming formulation including no less than 95 wt % water, a quaternary ammonium compound, and a foam stabilizer. The foaming formulation is substantially free of $C_1$-$C_6$ alcohols.

The present disclosure is further directed to a foaming formulation including no less than 95 wt % water, benzalkonium chloride (BZK), and a foam stabilizer. The foaming formulation is substantially free of $C_1$-$C_6$ alcohols.

The present disclosure is further directed to a cleansing product including a dispenser and a foaming formulation. The dispenser includes non-aerosol pumps, aerosol sprays, bottles, and the like. The foaming formulation includes no less than 95 wt % water, a quaternary ammonium compound, and a foam stabilizer. The foaming formulation is substantially free of $C_1$-$C_6$ alcohols.

Other objects and features will be in part apparent and in part pointed out hereinafter.

DEFINITIONS

Within the context of this specification, each term or phrase below will include, but not be limited to, the following meaning or meanings:

(a) "Liquid formulation" refers to both liquid and gel formulations. Non-limiting examples of liquid foaming formulations of the present disclosure include wet wipe solutions, alcohol-free hand sanitizers, alcohol-free surface sanitizers, body cleansers, hair shampoos, and the like.

(b) "Foam stabilizer" describes a compound that increases the longevity of a foam in a user's hand beyond that of the usage of the foaming formulation alone.

DETAILED DESCRIPTION OF THE DISCLOSURE

The present disclosure is directed to a foaming formulation comprising a quaternary ammonium compound and a foam stabilizer. The foaming formulation provides effective cleansing and/or sanitizing of an animate or inanimate surface without the use of $C_1$-$C_6$ alcohols. Further, the foaming formulation has an improved foaming effect, while further having improved aesthetics and skin-feel. Surprisingly, the formulation has improved foam stability as compared to foaming formulations including other alternatives to alcohol.

The foaming formulations of the present disclosure include a quaternary ammonium compound. Suitable examples of quaternary ammonium compounds for use in the present disclosure include, but are not limited to, benzalkonium chloride (BZK), stearalkonium chloride, benzethonium chloride, and combinations thereof.

The foaming formulations include the quaternary ammonium compound in amounts of from about 0.08% by weight to about 0.25% by weight, including from about 0.10% by weight to about 0.20% by weight, and including from about 0.10% by weight to about 0.15% by weight. In one suitable embodiment, the foaming formulation includes about 0.13% by weight benzalkonium chloride.

The foaming formulations of the present disclosure also include a foam stabilizer. Suitable foam stabilizers include compounds that increase the longevity of a foam in the hand of a user beyond the length of time when the foaming formulation is used alone. Specifically, for a foaming formulation to remain in the foam phase, bubbles in the foam must maintain their shape and volume without drainage. When drainage occurs, liquid from the outer portion, or skin, of the bubbles drains through the foam due to gravity and the bubbles cease to exist from the top down. As the foam volume decreases, the balance of the formulation begins pooling under the remaining foam as liquid until no more bubbles exist and liquid is all that remains.

Suitable examples of foam stabilizers for use in the present disclosure include, but are not limited to, polyethylene oxide, cationic guar gum, cationic cellulose, polyquaternium-2, polyquaternium-4, polyquaternium-6, polyquaternium-7, polyquaternium-10, polyquaternium-11, polyquaternium-15, polyquaternium-16, polyquaternium-22, polyquaternium-42, and combinations thereof. In a particularly suitable embodiment, the foam stabilizer is polyethylene oxide having a molecular weight of greater than 100,000 Daltons, such as POLYOX™ WSR (available from The Dow Chemical Company, Midland, Mich.). Other suitable examples of foam stabilizers can be found, for example, in U.S. Pat. No. 7,670,615 and U.S. Pub. No. 2008/0207767, both of which are incorporated herein by reference to the extent they are consistent herewith.

The foaming formulations include the foam stabilizer in amounts of from about 0.01% by weight to about 1.00% by weight, including from about 0.10% by weight to about 0.80% by weight, and including about 0.15% by weight.

In particularly suitable embodiments, the foaming formulation is in the form of a liquid formulation including no less than 90% by weight water, including no less than 93% by weight water, including no less than 95% by weight water, including no less than 96% by weight water, including no less than 97% by weight water, including no less than 98% by weight water, and including no less than 99% by weight water. In one suitable embodiment, the foaming formulation includes water in an amount such that the viscosity of the foaming formulation is less than 100 centipoise.

In some embodiments, the foaming formulation may also include various optional agents to modify the physical, chemical, hedonic or processing characteristics of the formulations or serve as beneficial agents when used for a targeted purpose or in a targeted user population. The optional agents include, for example, water-soluble emollients, humectants, moisturizers, botanicals, vitamins, non-aqueous solvents, preservatives, pH modifiers, sequestrants, antioxidants, anti-reddening agents, astringents, deodorants, external analgesics, film formers, fragrances, hydrotropes, skin conditioning agents, skin exfoliating agents, skin protectants, and the like.

Generally, water-soluble emollients lubricate, soothe, and soften the skin surface. Exemplary water-soluble emollients include ethoxylated or propoxylated oily or waxy ingredients such as esters, ethers, fatty alcohols, hydrocarbons, lanolin, and the like, and combinations thereof.

Particular water-soluble emollients could include, but are not to be limited to, PEG-7 glyceryl cocoate, PEG-6 caprylic/capric glycerides, hydrolyzed jojoba esters, the Hydramol™ product line from Lubrizol Corporation (Wickliffe, Ohio), the Resplanta® line of products from Res Pharma (Italy), and the like. One skilled in the art will recognize that this list is not all inclusive and could include any other suitable materials commonly known in the art or referenced in the Personal Care Products Council (PCPC) Compilation of Ingredients Used in Cosmetics in the United States (CIUCUS).

Humectants are hydroscopic agents that are widely used as moisturizers. Their function is to prevent the loss of moisture from the skin and to attract moisture from the environment. Common humectants include, for example, glycerin, propylene glycol, butylene glycol, betaine, sodium hyaluronate, sorbitol, urea, hydroxyethyl urea, and the like, and combinations thereof.

Furthermore, the formulation may include foam builders, such as, cocamidopropyl PG-dimonium chloride phosphate, lauramidopropyl PG-dimonium chloride, meadowfoamamidopropyl PG-dimonium chloride, myristamidopropyl PG-dimonium chloride phosphate, palmitamidopropyltrimonium chloride, sodium cocoamphoacetate, disodium cocoamphodiacetate, and combinations thereof.

Another additive for use in the formulation may be one or more non-aqueous solvents. Although not required, non-aqueous solvents may aid in dissolving certain components (e.g., preservatives, etc.). Examples of some suitable non-aqueous solvents include, but are not limited to, glycerin, glycols, such as propylene glycol, butylene glycol, triethylene glycol, hexylene glycol, polyethylene glycol monoalkyl ethers, ethoxydiglycol, and dipropyleneglycol, and combinations thereof.

Preservatives for increasing the shelf life of the formulations may also be used. Exemplary suitable preservatives include, but are not limited to, Kathon™ CG, which is a mixture of methylchloroisothiazolinone and methylisothiazolinone, available from Dow Chemical Company, Midland, Mich.; Mackstat® H 66, available from Rhodia, member of the Solvay Group, Bristol, Pa.; DMDM hydantoin (e.g., Glydant® Plus, Lonza, Inc., Switzerland); tetrasodium EDTA; iodopropynyl butylcarbamate; benzoic esters (parabens), such as methylparaben, propylparaben, butylparaben, ethylparaben, sodium methylparaben, and sodium propylparaben; phenoxyethanol; benzyl alcohol; phenethyl alcohol; 2-bromo-2-nitropropane-1,3-diol; benzoic acid; amidazolidinyl urea; diazolidinyl urea; and the like. Other suitable preservatives include those sold by Ashland Inc., Ashland, Ky., such as "Germall 115" (amidazolidinyl urea), "Germall II" (diazolidinyl urea), and "Germall Plus" (diazolidinyl urea and iodopropynyl butylcarbonate). Particularly suitable preservatives include Neolone™ CapG, which is a mixture of methylisothiazolinone and caprylyl glycol, available from Dow Chemical Company, Midland, Mich.; Symdiol® 68, which is a mixture of 1,2-hexanediol and caprylyl glycol, available from Symrise, Teterboro, N.J.; and Lexgard® O, which is caprylyl glycol, available from Inolex Chemical Company, Philadelphia, Pa.

Suitable skin conditioning agents for use in the foaming formulations include skin conditioning agents known in the art. Particularly suitable skin conditioning agents include, for example, hydrolyzed plant proteins such as hydrolyzed wheat protein, hydrolyzed soy protein, hydrolyzed collagen, and the like.

In general, the pH of the foaming formulations may be controlled to be within any desired range, depending on the targeted use. By way of example, for bodily cleansing, it is typically desirable to have a foaming formulation with a slightly acidic to neutral pH. If necessary, various pH modifiers may be utilized in the foaming formulation to achieve the desired pH level. For instance, some examples of basic pH modifiers that may be used in the formulations of the present disclosure include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine.

Moreover, some examples of acidic pH modifiers that may be used in the formulations of the present disclosure include, but are not limited to, mineral acids; carboxylic acids; and polymeric acids. Specific examples of suitable mineral acids are hydrochloric acid, nitric acid, phosphoric acid, and sulfuric acid. Specific examples of suitable carboxylic acids are acetic acid, tartaric acid, citric acid, glycolic acid, lactic acid, maleic acid, malic acid, succinic acid, glutaric acid, benzoic acid, malonic acid, salicylic acid, gluconic acid, and mixtures thereof. Specific examples of suitable polymeric acids include carrageenic acid, humic acid, fulvic acid, and alginic acid.

In one embodiment, the foaming formulation may additionally include one or more sequestrants. A sequestrant is a substance whose molecules can form one or more bonds with a metal ion. In particular, water that may be contained in the foaming formulation often contains metal ions, such as calcium ions, that might react with anionic components (e.g., acids) present within the foaming formulation. For example, in one embodiment, an anionic component that remains substantially unreacted with metal ions can better function as a cleansing agent. Some examples of sequestrants that may be used in the foaming formulations of the present disclosure include, but are not limited to, ethylenediamines, ethylenediaminetetraacetic acids (EDTA) acid and/or salts thereof, citric acids and/or salts thereof, glucuronic acids and/or salts thereof, iminodisuccinic acid and/or salts thereof, polyphosphates, organophosphates, dimercaprols, and the like.

Still other optional agents include: antioxidants (product integrity); anti-reddening agents, such as aloe extract; astringents—cosmetic (induce a tightening or tingling sensation on skin); astringents—drug (a drug product which checks oozing, discharge, or bleeding when applied to skin or mucous membrane and works by coagulating protein); botanicals (e.g., Actiphyte of Aloe Vera 10 Fold GL, Actiphyte of Cucumber GL, Actiphyte of Japanese Green Tea GL, all from The Lubrizol Corporation, Wickliffe, Ohio); vitamins (e.g., tocopheryl acetate, retinyl palmitate, panthenol, ascorbic acid); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); fragrances (consumer appeal); hydrotropes (helps dissolve some anti-microbial agents); and skin protectants (a drug product which protects injured or exposed skin or mucous membrane surface from harmful or annoying stimuli).

The amounts of the optional components will depend on the formulation to be prepared and the amounts of the other components in the foaming formulation.

The foaming formulations of the present disclosure are substantially free of $C_1$-$C_6$ alcohols. In this context, and unless otherwise specified, the term "substantially free" means that the foaming formulations contain less than a functional amount of $C_1$-$C_6$ alcohols, typically less than 0.10, including less than 0.050, including less than 0.0150, including less than 0.0010, and also including zero percent, by weight of $C_1$-$C_6$ alcohols.

In some embodiments, the foaming formulations are substantially free of anionic and/or nonionic surfactants. Anionic surfactants are defined as those surfactants that possess a negative charge and include such surfactant classes as sulfates, sulfonates, sulfosuccinates, taurates, isethionates, alkanoic acids, ester carboxylic acids and ether carboxylic acids. Nonionic surfactants are defined as those surfactants possessing no charge moieties within the molecular structure and include such surfactant classes as alkanolamides, ethoxylated amides, ethoxylated fatty acids, ethoxylated fatty alcohols, alkoxylated esters, alkyl polyglucosides, alkoxylated triglycerides, sorbitan esters and sorbitan ethers. In this context, and unless otherwise specified, the term "substantially free" means that the foaming formulations contain less than a functional amount of anionic and/or nonionic surfactants, typically less than 0.1%, including less than 0.05%, including less than 0.015%, including less than 0.001%, and also including zero percent, by weight of anionic and/or nonionic surfactants.

Methods of Preparing the Formulations

The foaming formulations are generally prepared by mixing all components together to form a homogeneous solution. Typically, the foaming formulation is prepared by mixing the quaternary ammonium compound and foam stabilizer, typically with water, and with any further optional agents minimizing aeration. In one embodiment, the quaternary ammonium compound and foam stabilizer are mixed with water and any additional components at room temperature.

While used as a liquid formulation, any solid components are first completely dissolved in water or other solvents before mixing with other components. The liquid foaming formulations can be dispensed from a non-aerosol pump or aerosol spray as generally available in the art. In addition, the liquid formulation may be used as a leave-on lotion, gel or rinse.

Cleansing Products Including the Foaming Formulation

While capable of being applied directly to the skin or an inanimate surface, such as in the form of a lotion, gel, spray, rinse, or the like, in some embodiments, the foaming formulations may be applied to one or more substrates to provide for a cleansing product, such as a wipe, wrap (e.g., medical wraps and bandages), and the like. As used herein, the term "cleansing product" refers to both a cleansing product and/or a sanitizing product. Wipes including the foaming formulation can be wet wipes or dry wipes. As used herein, the term "wet wipe" means a wipe that includes greater than 70% (by weight substrate) moisture content. As used herein, the term "dry wipe" means a wipe that includes less than 10% (by weight substrate) moisture content. When a dry wipe is to be used for cleansing, the wipe is typically wetted with an aqueous solution prior to using the wipe to solubilize the quaternary ammonium compound to provide for the foaming effects. Specifically, suitable wipes for including the foaming formulation can include wet wipes, hand wipes, face wipes, cosmetic wipes, household wipes, industrial wipes, and the like. Particularly preferred wipes are wet wipes, such as baby wipes and perineal wipes.

Materials suitable for the substrate of the wipes are well known to those skilled in the art, and are typically made from a fibrous sheet material which may be either woven or non-woven as described more fully in U.S. Pat. No. 4,100,324, issued to Anderson, et al. (Jul. 11, 1978); U.S. Pat. No. 5,284,703, issued to Everhart, et al. (Feb. 8, 1994); and U.S. Pat. No. 5,350,624, issued to Georger, et al. (Sep. 27, 1994), which are incorporated by reference to the extent to which they are consistent herewith.

Typically, when used with a substrate material, the cleansing products include the foaming formulation in an add-on amount of from about 150% by weight to about 600% by weight dry basesheet, including from about 175% by weight to about 450% by weight dry basesheet, and including from about 200% by weight to about 400% by weight dry basesheet.

Methods of Use

The foaming formulations of the present disclosure can be used to provide effective cleansing and/or sanitizing of animate and inanimate surfaces. In one embodiment, the foaming formulations may be used to sanitize a user's body. These foaming formulations are capable of being topically applied to the skin of a user to kill and/or inhibit the growth of bacteria and other microorganisms on the skin, particularly, on the hands, arms, and face of a user. In one suitable embodiment, the foaming formulation is capable of providing at least a 4 log reduction, including greater than 3 log reduction, of S. aureus ATCC 6538, E. coli ATCC 11229, S. aureus ATCC 33591, B. cepacia ATCC 35416, P. aeruginosa ATCC 15442, and C. albicans ATCC 10231 within 15 seconds after contact using ASTM E2315-03 NG3571.

Moreover, the foaming formulations provide a sanitizing effect without the use of irritating components such as $C_1$-$C_6$ alcohols. Accordingly, the user can effectively sanitize the body without irritation and skin damage.

The foaming formulations have improved stability such that the foaming formulations provide a sanitizing effect for a sufficiently long period of time in order to effectively remove dirt and microorganisms. The foaming formulations have improved aesthetics (e.g., soft feel, improved foam appearance (e.g., even dispersion of foam from a dispensing device, smaller, more densely packed gas bubbles having uniform size and density, gas bubbles that do not degrade or convert quickly to a bubbly liquid)) and skin-feel.

Having described the disclosure in detail, it will be apparent that modifications and variations are possible without departing from the scope of the disclosure defined in the appended claims.

EXAMPLES

The following non-limiting Examples are provided to further illustrate the present disclosure.

Example 1

In this Example, a suitable foaming formulation of the present disclosure was prepared for use as a liquid hand cleanser. The components of the formulation are shown in the table below.

| Component | INCI Name | Wt % |
|---|---|---|
| Water | Water | 98.56 |
| Neolone ™ CapG (The Dow Chemical Company, Midland, MI) | Caprylyl Glycol, Methylisothiazolinone | 0.83 |
| Colalipid C (Colonial Chemical, Inc., South Pittsburg, TN) | Cocamidopropyl PG-Dimonium Chloride Phosphate | 0.30 |
| POLYOX ™ WSR 205 (The Dow Chemical Company, Midland, MI) | Polyethylene Oxide | 0.05 |
| Stepanquat ® NF 50 (Stepane Company, Northfield, IL) | Benzalkonium Chloride (50 wt %) | 0.26 |
| Citric acid | Citric Acid | to pH 6.5 |

To prepare the foaming formulation, water was first added to a vessel. While stirring the water, POLYOX™ WSR 205 was slowly added to the vortex and mixed until completely dissolved. The Neolone™ CapG, Colalipid C, and Stepanquat® NF 50 were added to the solution one at a time waiting for the first to incorporate completely before adding the next. Finally, citric acid was added to reach a final pH of approximately 6.5, and the mixture was mixed to homogeneity at room temperature.

Example 2

In this Example, a suitable foaming formulation of the present disclosure was prepared for use as an alcohol-free foaming hand sanitizer. The components of the formulation are shown in the table below.

| Component | INCI Name | Wt % |
|---|---|---|
| Water |  | 98.56 |
| Mackam ® 1C (Rhodia Inc., Cranbury, NJ) | Sodium cocoamphoacetate | 0.3 |
| Neolone ™ CapG (The Dow Chemical Company, Midland, MI) | Caprylyl Glycol, Methylisothiazolinone | 0.83 |
| POLYOX ™ WSR 205 (The Dow Chemical Company, Midland, MI) | Polyethylene Oxide | 0.05 |
| Stepanquat ® NF 50 (Stepane Company, Northfield, IL) | Benzalkonium Chloride (50 wt %) | 0.26 |
| Citric Acid | Citric Acid | to pH 6.5 |

To prepare the foaming formulation, water was first added to a vessel. While stirring the water, POLYOX™ WSR 205 was slowly added to the vortex and mixed until completely dissolved. The Neolone™ CapG, Mackam® 1C, and Stepanquat® NF 50 were added to the solution one at a time waiting for the first to incorporate completely before adding the next.

Finally, citric acid was added to reach a final pH of approximately 6.5, and the mixture was mixed to homogeneity at room temperature.

Example 3

In this Example, several suitable foaming formulations of the present disclosure were prepared using the method of Example 1 for use as foaming hand sanitizers. Many preservative systems were evaluated. The components of the formulations are shown in the table below.

| Component | INCI Name | A | B | C | D | E | F | G |
|---|---|---|---|---|---|---|---|---|
| | | | | | Wt % | | | |
| Water | Water | 99.39 | 98.29 | 98.29 | 98.89 | 98.9 | 98.6 | 98.56 |
| Neolone ™ CapG (The Dow Chemical Company, Midland, MI) | Caprylyl Glycol, Methylisothiazolinone | 0.83 | 1.1 | | | 0.83 | 1.1 | |
| Benzostat ™ (Inolex, Philadelphia, PA) | Caprylhydroxamic Acid (and) Benzyl Alcohol (and) Glycerine | | | 1.1 | | | | |
| Mackstat ® SHG (Rhodia Inc., Cranbury, New Jersey) | Sodium Hydroxymethylglycinate | | | | 0.5 | | | |
| Propylene Glycol USP (Arch Chemical, Norwalk, CT) | Propylene Glycol | | | | | | | 0.33 |
| Lexgard ® O (Inolex, Philadelphia, PA) | Caprylyl Glycol | | | | | | | 0.50 |
| Colalipid C (Colonial Chemical, Inc., South Pittsburg, TN) | Cocamidopropyl PG-Dimonium Chloride Phosphate | 0.30 | 0.30 | 0.30 | — | — | — | 0.30 |
| POLYOX ™ WSR 205 (The Dow Chemical Company, Midland, MI) | Polyethylene Oxide | 0.05 | 0.05 | 0.05 | 0.05 | 0.05 | 0.05 | 0.05 |
| Stepanquat ® NF 50 (Stepane Company, Northfield, IL) | Benzalkonium Chloride (50 wt %) | 0.26 | 0.26 | 0.26 | 0.26 | 0.26 | 0.26 | 0.26 |
| Citric acid | Citric Acid | to pH 6.5 | to pH 6.5 | to pH 6.5 | to pH 6.5 | to pH 6.5 | to pH 6.5 | to pH 6.5 |

Example 4

In this Example, selected compositions of the Example 3 were tested using ASTM E 2315 (Suspension Time-Kill) to display antimicrobial efficacy. Summarized results of ASTM E 2315 are displayed in the table below.

| Code | Organism | Contact Time | CFU/ml | Log Reduction from Time Zero |
|---|---|---|---|---|
| A | E. coli ATCC 11229 | Time Zero | 2.10E±05 | N/A |
| | | 15 Seconds | <5 | >4.62 |
| | | 30 Seconds | <5 | >4.62 |
| | | 45 seconds | <5 | >4.62 |
| | S. aureus ATCC 6538 | Time Zero | 1.80E±05 | N/A |
| | | 15 Seconds | <5 | >4.56 |
| | | 30 Seconds | <5 | >4.56 |
| | | 45 seconds | <5 | >4.56 |
| | S. aureus ATCC 33591 | Time Zero | 1.10E±05 | N/A |
| | | 15 Seconds | <5 | >4.34 |
| | (MRSA) | 30 Seconds | <5 | >4.34 |
| | | 45 seconds | <5 | >4.34 |
| | B. Cepacia ATCC 25416 | Time Zero | 2.30E±05 | N/A |
| | | 15 Seconds | <5 | >4.66 |
| | | 30 Seconds | <5 | >4.66 |
| | | 45 seconds | <5 | >4.66 |
| | P. aeruginosa ATCC 15442 | Time Zero | 2.15E±05 | N/A |
| | | 15 Seconds | <5 | >4.63 |
| | | 30 Seconds | <5 | >4.63 |
| | | 45 seconds | <5 | >4.63 |

-continued

| Code | Organism | Contact Time | CFU/ml | Log Reduction from Time Zero |
|---|---|---|---|---|
|  | C. albicans ATCC 10231 | Time Zero | 3.15E±05 | N/A |
|  |  | 15 Seconds | <5 | >4.80 |
|  |  | 30 Seconds | <5 | >4.80 |
|  |  | 45 seconds | <5 | >4.80 |
| B | E. coli ATCC 11229 | Time Zero | 2.10E±05 | N/A |
|  |  | 15 Seconds | <5 | >4.62 |
|  |  | 30 Seconds | <5 | >4.62 |
|  |  | 45 seconds | <5 | >4.62 |
|  | S. aureus ATCC 6538 | Time Zero | 1.80E±05 | N/A |
|  |  | 15 Seconds | <5 | >4.56 |
|  |  | 30 Seconds | <5 | >4.56 |
|  |  | 45 seconds | <5 | >4.56 |
|  | S. aureus ATCC 33591 (MRSA) | Time Zero | 1.10E±05 | N/A |
|  |  | 15 Seconds | <5 | >4.34 |
|  |  | 30 Seconds | <5 | >4.34 |
|  |  | 45 seconds | <5 | >4.34 |
|  | B. Cepacia ATCC 25416 | Time Zero | 2.30E±05 | N/A |
|  |  | 15 Seconds | <5 | >4.66 |
|  |  | 30 Seconds | <5 | >4.66 |
|  |  | 45 seconds | <5 | >4.66 |
|  | P. aeruginosa ATCC 15442 | Time Zero | 2.15E±05 | N/A |
|  |  | 15 Seconds | <5 | >4.63 |
|  |  | 30 Seconds | <5 | >4.63 |
|  |  | 45 seconds | <5 | >4.63 |
|  | C. albicans ATCC 10231 | Time Zero | 3.15E±05 | N/A |
|  |  | 15 Seconds | <5 | >4.80 |
|  |  | 30 Seconds | <5 | >4.80 |
|  |  | 45 seconds | <5 | >4.80 |
| D | E. coli ATCC 11229 | Time Zero | 2.10E±05 | N/A |
|  |  | 15 Seconds | <5 | >4.62 |
|  |  | 30 Seconds | <5 | >4.62 |
|  |  | 45 seconds | <5 | >4.62 |
|  | S. aureus ATCC 6538 | Time Zero | 1.80E±05 | N/A |
|  |  | 15 Seconds | <5 | >4.56 |
|  |  | 30 Seconds | <5 | >4.56 |
|  |  | 45 seconds | <5 | >4.56 |
|  | S. aureus ATCC 33591 (MRSA) | Time Zero | 1.10E±05 | N/A |
|  |  | 15 Seconds | <5 | >4.34 |
|  |  | 30 Seconds | <5 | >4.34 |
|  |  | 45 seconds | <5 | >4.34 |
|  | B. Cepacia ATCC 25416 | Time Zero | 2.30E±05 | N/A |
|  |  | 15 Seconds | <5 | >4.66 |
|  |  | 30 Seconds | <5 | >4.66 |
|  |  | 45 seconds | <5 | >4.66 |
|  | P. aeruginosa ATCC 15442 | Time Zero | 2.15E±05 | N/A |
|  |  | 15 Seconds | <5 | >4.63 |
|  |  | 30 Seconds | <5 | >4.63 |
|  |  | 45 seconds | <5 | >4.63 |
|  | C. albicans ATCC 10231 | Time Zero | 3.15E±05 | N/A |
|  |  | 15 Seconds | <5 | >4.80 |
|  |  | 30 Seconds | <5 | >4.80 |
|  |  | 45 seconds | <5 | >4.80 |
| F | E. coli ATCC 11229 | Time Zero | 2.10E±05 | N/A |
|  |  | 15 Seconds | <5 | >4.62 |
|  |  | 30 Seconds | <5 | >4.62 |
|  |  | 45 seconds | <5 | >4.62 |
|  | S. aureus ATCC 6538 | Time Zero | 1.80E±05 | N/A |
|  |  | 15 Seconds | <5 | >4.56 |
|  |  | 30 Seconds | <5 | >4.56 |
|  |  | 45 seconds | <5 | >4.56 |
|  | S. aureus ATCC 33591 (MRSA) | Time Zero | 1.10E±05 | N/A |
|  |  | 15 Seconds | <5 | >4.34 |
|  |  | 30 Seconds | <5 | >4.34 |
|  |  | 45 seconds | <5 | >4.34 |
|  | B. Cepacia ATCC 25416 | Time Zero | 2.30E±05 | N/A |
|  |  | 15 Seconds | <5 | >4.66 |
|  |  | 30 Seconds | <5 | >4.66 |
|  |  | 45 seconds | <5 | >4.66 |
|  | P. aeruginosa ATCC 15442 | Time Zero | 2.15E±05 | N/A |
|  |  | 15 Seconds | <5 | >4.63 |
|  |  | 30 Seconds | <5 | >4.63 |
|  |  | 45 seconds | <5 | >4.63 |
|  | C. albicans ATCC 10231 | Time Zero | 3.15E±05 | N/A |
|  |  | 15 Seconds | 2.55E±02 | 3.09 |
|  |  | 30 Seconds | 1.00E±01 | 4.50 |
|  |  | 45 seconds | <5 | >4.80 |

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above formulations and cleansing products without departing from the scope of the disclosure, it is intended that all matter contained in the above description shall be interpreted as illustrative and not in a limiting sense.

What is claimed is:

1. A foaming formulation comprising no less than 95 wt % water, from about 0.10 wt % to about 0.15 wt % of a quaternary ammonium compound and from about 0.01 wt % to about 1.00 wt % of a foam stabilizer, wherein the quaternary ammonium compound is benzalkonium chloride and the foam stabilizer consists of polyethylene oxide, and wherein the foaming formulation is substantially free of $C_1$-$C_6$ alcohols.

2. The foaming formulation of claim 1 further comprising a preservative.

3. The foaming formulation of claim 1 further comprising a foam builder.

4. The foaming formulation of claim 3 wherein the foam builder is selected from the group consisting of cocamidopropyl PG-dimonium chloride phosphate, lauramidopropyl PG-dimonium chloride, meadowfoamamidopropyl PG-dimonium chloride, myristamidopropyl PG-dimonium chloride phosphate, palmitamidopropyltrimonium chloride, sodium cocoamphoacetate, disodium cocoamphodiacetate, and combinations thereof.

5. The foaming formulation of claim 1 further comprising a pH modifier.

6. The foaming formulation of claim 1 further comprising at least one agent selected from the group consisting of water-soluble emollients, humectants, moisturizers, botanicals, vitamins, non-aqueous solvents, preservatives, pH modifiers, sequestrants, antioxidants, anti-reddening agents, astringents, deodorants, external analgesics, film formers, fragrances, hydrotropes, opacifiers, skin conditioning agents, and skin protectants.

7. The foaming formulation of claim 1 having at least a 4 log reduction of S. aureus ATCC 6538, E. coli ATCC 11229, S. aureus ATCC 33591, B. cepacia ATCC 35416, P. aeruginosa ATCC 15442, and C. albicans ATCC 10231 within 15 seconds after contact.

8. The foaming formulation of claim 1 comprising at least 98 wt % water.

9. A foaming formulation comprising no less than 95 wt % water, from about 0.10 wt % to about 0.15 wt % of benzalkonium chloride; and from about 0.01 wt % to about 0.15 wt % of a foam stabilizer, wherein the foam stabilizer consists of polyethylene oxide, and wherein the foaming formulation is substantially free of $C_1$-$C_6$ alcohols.

10. A cleaning product comprising a dispenser and a foaming formulation, the foaming formulation comprising no less than 95 wt % water, from about 0.10 wt % to about 0.15 wt % of a quaternary ammonium compound and from about 0.01 wt % to about 1.00 wt % of a foam stabilizer, wherein the quaternary ammonium compound is benzalkonium chloride and the foam stabilizer consists of polyethylene oxide, and wherein the foaming formulation is substantially free of $C_1$-$C_6$ alcohols.

11. The cleansing product of claim 10 wherein the dispenser is selected from the group consisting of non-aerosol pump, aerosol spray, and bottle.

12. The cleansing product of claim 10 wherein the quaternary ammonium compound is selected from the group consisting of benzalkonium chloride, stearalkonium chloride, benzethonium chloride, and combinations thereof.

13. The foaming formulation of claim 9, wherein the polyethylene oxide is present in an amount of about 0.05% by weight of the formulation.

14. The cleaning product of claim 10, wherein the polyethylene oxide is present in an amount of from about 0.01% by weight to about 0.15% by weight of the formulation.

15. The foaming formulation of claim 1, wherein the polyethylene oxide is present in an amount of about 0.05% by weight of the formulation.

16. The cleaning product of claim 10, wherein the polyethylene oxide is present in an amount of about 0.05% by weight of the formulation.

17. The foaming formulation of claim 1, wherein the benzalkonium chloride is present in an amount of about 0.13% by weight of the formulation.

18. The foaming formulation of claim 9, wherein the benzalkonium chloride is present in an amount of about 0.13% by weight of the formulation.

19. The cleaning product of claim 10, wherein the benzalkonium chloride is present in an amount of about 0.13% by weight of the formulation.

20. The foaming formulation of claim 4, wherein the foam builder is present in an amount of from about 0.1% by weight to about 0.5% by weight of the formulation.

* * * * *